United States Patent [19]

Hayashi

[11] Patent Number: 4,821,080

[45] Date of Patent: Apr. 11, 1989

[54] MEASURING APPARATUS FOR ENZYME REACTION RATES

[75] Inventor: Hidechika Hayashi, Yokohama, Japan

[73] Assignee: Tosoh Corporation, Shinnanyo, Japan

[21] Appl. No.: 152,104

[22] Filed: Feb. 4, 1988

[30] Foreign Application Priority Data

Feb. 10, 1987 [JP] Japan .................................. 62-29298

[51] Int. Cl.$^4$ ............................................ G01N 21/64
[52] U.S. Cl. .................................. 356/318; 250/458.1; 356/417
[58] Field of Search ...................... 356/317, 318, 417; 250/458.1, 459.1, 461.1

[56] References Cited

U.S. PATENT DOCUMENTS 4,495,293 1/1985 Shaffar .............................. 250/461.1
4,626,684 12/1986 Landa ................................ 250/461.1

Primary Examiner—Vincent P. McGraw
Attorney, Agent, or Firm—Oblon, Fisher, Spivak, McClelland & Maier

[57] ABSTRACT

A measuring apparatus for enzyme reaction rates comprising optical detection means for detecting in time series the intensity of fluorescence derived from fluorescent materials obtained through enzyme reactions, a first arithmetic circuit having time series signals of the intensity of the fluorescence detected by the optical detection means as an input for calculating apparent increasing rate of the fluorescent materials by utilizing a predetermined computation equation, and a second arithmetic circuit having an apparent increasing rate of the fluorescent materials computed through the first arithmetic circuit as an input information for calculating a true increasing rate of the fluorescent materials by utilizing a predetermined correction equation, wherein enzyme contributing to the aforementioned reaction is obtained through enzyme immunoreaction.

2 Claims, 4 Drawing Sheets

MEASURING APPARATUS FOR ENZYME REACTION RATES

BACKGROUND OF THE INVENTION

1. Field of the Invention

This invention relates to a measuring apparatus for measuring enzyme reaction rate on the basis of the detected information of the intensity of fluorescence such as increasing rate of the intensity of fluorescence emitted from the fluorescent materials produced by enzymatic reactions, and more particularly to a measuring apparatus for enzyme immunoassay for favorably determining the quantity of the biological active materials.

2. Description of the Related Art

Conventionally, as one of enzyme assays to detect or measure the quantity of enzyme, one method is known to measure the rate of enzyme reactions on the basis of detecting decreasing rate of photo absorption and fluorescence of enzyme substrates in the sample derived from enzyme reactions or increasing rate of photo absorption and fluorescence derived from enzyme reaction products. Generally, a method to detect the absorption of light is used in most cases. However, fluorometry is often used for measuring a very small quantity of enzyme.

Especially, in an automated equipment for immunoassay which has been introduced recently with the aim of detecting or determining micro constituents in biological samples, that is, in the equipment on the basis of so called enzyme immunoassay, wherein very small quantity of physiologically active materials is linked with enzyme by immunoreactions, and the linked quantity of enzyme is measured, fluorometry is used in most cases for the necessity of measuring very small quantity of enzyme.

In the fluorometry, for example, in order to measure the quantity of fluorescent materials, the fluorometer is generally used, wherein included are an applied light system to excite samples including the fluorescent materials for measuring such as the quantity of the fluorescent materials, a measuring system of the received light to detect and measure the intensity of fluorescence by receiving the fluorescent light emitted from the fluorescent materials, and a data processor to determine the rate of the enzyme reaction from the variations of the intensity of fluorescence as the actual information.

In the aforementioned conventional apparatus for measuring the rate of enzyme reactions, especially the data processor thereof, it is common to measure the quantity or density of the fluorescent materials by using a known conversion equation on the basis of data (the intensity of fluorescence) obtained from actual measurement through the aforementioned measuring system of the received light, and further from the quantitative variations (or the variations in density), to finally calculate the reaction rate of enzyme through linear regression using a method of least squares. However, in this kind of measurement, some problems may occur due to the error in measured rate of enzyme reactions caused by the absorption of the excited light into fluorescent materials.

When the density is low in fluorescent materials and under the conditions where there are fairly few degrees of the absorption of the excited light by the fluorescent materials, it may be said that there will be few problems on the errors in the measured results of the rate of enzyme reaction calculated by the aforementioned formula, but on the other hand, under the conditions where the density of fluorescent materials is high and the ratio of the absorption of the excited light becomes larger than several percentages, it will be difficult to determine the exact measurement values by calculating the rate of enzyme reactions from the intensity of fluorescence on the basis of the aforementioned linear equation, thereby necessitates the elimination of the errors caused by the absorption of the excited light for obtaining the exact results of the measurement.

SUMMARY OF THE INVENTION

It is an object of the present invention which has been made from the viewpoints described above to provide a measuring apparatus for the reaction rate of enzyme capable of measuring exactly ranging from the low reaction rate of enzyme to the high reaction rate of enzyme in the measurement of the reaction rate of enzyme.

Another object of this invention is to provide a measuring apparatus for enzyme reaction rates of a structure to favorably match the measuring apparatus with the actual use, especially to alleviate the burdens of the data processor.

DETAILED DESCRIPTION OF THE INVENTION

Figure 1:
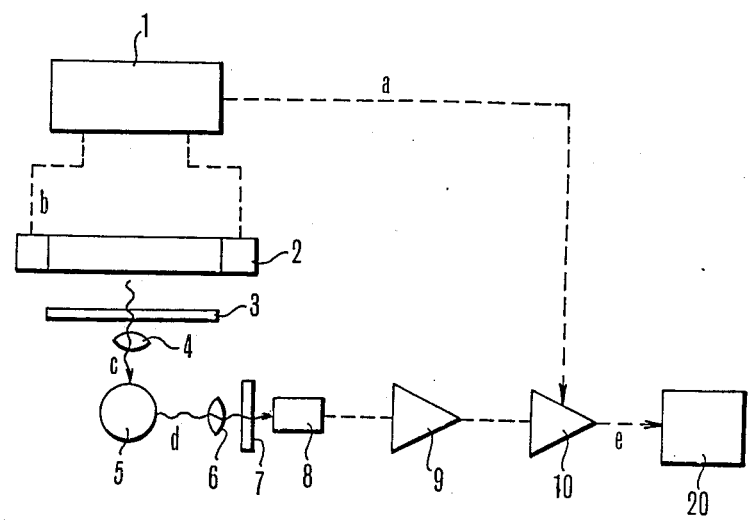
FIG. 1 is a drawing illustrating one example of the structural summary of the measuring apparatus for enzyme reaction rates of this invention.

Under the foregoing objects, however, one of the embodiments of the present invention is a measuring apparatus for enzyme reaction rates, comprising an optical detecting means for detecting in time series the intensity of fluorescence derived from fluorescent materials obtained through enzyme reactions, a first arithmetic circuit having the time series signals of the intensity of the fluorescence detected by the optical detection means as an input for calculating apparent increasing rate of the fluorescent materials by utilizing the predetermined computation equation, and a second arithmetic circuit having apparent increasing rate of the fluorescent materials computed through the first arithmetic circuit as an input information for calculating true increasing rate of the fluorescent materials by utilizing the predetermined correction equations.

The reason for having adopted the structure mentioned above in order to attain the object of the present invention will be clearly disclosed by the following.

When constructing a measuring apparatus for enzyme reaction rates suitable for actual use, it is desirable that the measuring apparatus should be automated as much as possible and the finally measured results should be outputted in a favorable modes of utilization for measuring and processing many samples quickly and efficiently. It is also desirable that such an apparatus should be structure in simple and small sized and low costly for wider utilization. These are common problems generally demanded for machinery.

On the other hand, in order to decrease the above mentioned influence on the error of the measured value as far as possible in the apparatus of the present invention, it is necessary to calculate, for instance, not the quantity of fluorescent materials (or density) simply (that is to say, without any consideration for the error derived from the absorption of the excited light) from the detected information of the intensity of fluorescence by the optical system, but the reaction rate of enzyme corrected for the error derived from the absorption of the excited light. However, such error corrections are liable to be led to the need of a large size data processor (such as the increase in the number of operations in case of the utilization of micro computers, the need for large sized CPU and memory system) and increase in cost.

Therefore in the present invention, the measured results having least influence on the measured error can be obtained as far as possible, and moreover, the apparatus of the present invention with the above mentioned construction has been provided as having small sized structure and preferably in conformity with actual demand for small burdens on the data processor.

Concrete fundamental structure of the apparatus applicable to the measuring apparatus for enzyme reaction rates consisting of the present invention on the basis of the above mentioned viewpoints is described in the following. Typically, samples to be used in the present invention consist of enzyme and substrate solutions which are filled into a small container (cup) having, in general, a vacancy (called Cell) of inner capacity of several ml - dozens of ml or the cell of the plate wherein many cells are formed. Activating the enzyme causes to produce fluorescent materials in the substrate solution and to increase the intensity of fluorescence.

The enzyme described above is permissible in any form of, for instance, the enzyme fixed on a solid phase or in free conditions, or antigen-antibody reaction enzyme complex, showing enzyme activity. The applying system to illuminate the light source (the excited light) for detecting fluorescence from the sample is usually provided with a light source, a filter, a mirror, and a condenser lens. Generally, it is advisable to join a means for switching the light source illumination (the excited light) in addition to the applying system. As a switching means, rotating blades may be installed as a mechanical chopper in the light path of the applying system for interrupting the light intermittently. For ensuring long consecutive running and durability, it is desirable to use discharge tubes or fluorescent lamps for AC or pulse lighting. Switching of the illumination light (the excited light) for the sample is used to eliminate the influence of the background light when the measurement is performed. The degree of the switching depends on the lamp to be used, frequency characteristics of the amplifier of the measuring system for the received light, generally ranging from 10 Hz to several KHz in most preferred cases.

Needless to say, a light source of DC lighting system is used for the measurement within a black box.

Optical detecting means for detecting in time series the intensity of fluorescence, that is to say, the measuring system for the received light is usually provided as a combination of a mirror, a condenser lens, a filter, light receiving sensors such as a photodiode or a photo multiplier, an amplifier, an analog-digital converter and others. When switching the applying system to eliminate the background light as described above is required, a rectifier is added to the structure to make phase sensitive detection of electric signals from the light receiving sensor by using, for instance, clock signals of the applied voltage for the fluorescent tube as a light source of the excited light.

According to such a phase sensitive detection, the influence of outer lights is removed from the signals gained through the light receiving sensor and fluorescent component of the fluorescent materials in the sample depending on the source light are extracted, thereby making possible to detect the precise intensity of fluorescence (in this case the influence of the absorption of the excited light remains).

When the applying system is used as the light source for the DC lighting system, the process is not required for fluorescent (intensity) signals to be detected.

Such fluorescent (intensity) signals are fed, for instance, to the analog signal processing circuit (data processing circuit) or digital signal processing circuit (data processing circuit) after being converted into digital signals by the analog-digital converter, and are made into input signals (actual signals) of the data processor.

Figure 5:
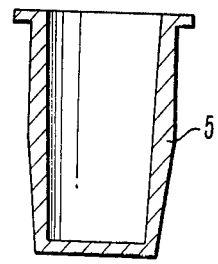
FIG. 5 is a vertical sectional view illustrating one example of the sample containers.

Furthermore, in order to typically detect fluorescence in the present invention, a top-to-top method is used, wherein the source light (the excited light) is radiated and the fluorescence is extracted in the same axis with the sample (from overhead, for instance, when a container shown on FIG. 5 is used), but the directions of the source light (the excited light) radiation and the fluorescence can be different. When the top-to-top method is adopted, efficient measurement is attainable by making optical measurement intermittently while carrying a lot of containers in line. And the method is specially suitable for the structure of the automated apparatus.

For example, in the optical structure for the top-to-top method described above, a half mirror or a dichroic mirror is installed in the optical path of the applying system from the horizontal side direction for radiating the source light into the container below (wherein samples are filled), from which the fluorescence is extracted and transmitted upward through the dichroic mirror for permitting the light receiving sensor to receive the light. The light applying and light receiving system are thus installed faced to corresponding containers of the samples.

Detection of fluorescence data (the intensity of fluorescence) in the samples in general is initiated promptly in conformity with the start of the enzyme reactions in the aforementioned container (or after a certain waiting time) and is finished after frequent sampling with small intervals over a prescribed range of time. Initiating and finishing time are determined depending on the type, density, required accuracy of the measurement, conditions of the reaction progress for the samples (enzymes, substrates) to be measured.

According to the present invention, the data of the intensity of fluorescence obtained by the aforementioned method is put into the first arithmetic circuit. Then the data in the original conditions or after being converted into the quantity of the fluorescence materials is used for calculating the increasing rate of the fluorescent materials by the linear regression using the least squares method and for determining the background quantity of the fluorescent materials at the time of the initiating time of enzyme reactions (zero time).

Accordingly, the increasing rate of the fluorescent materials obtained from the first arithmetic circuit is the apparent value, in which the absorption of the excited light by fluorescent materials is not corrected. The operation is performed within a prescribed time of measurement.

After the accomplishment of the actual measuring, the data processor in the present invention corrects the error caused by the absorption of the excited light and calculates the true increasing rate of the fluorescent materials with the second arithmetic circuit on the basis of the apparent increasing rate of fluorescent materials obtained through the first arithmetic circuit described above.

Correction factors of the data correction process in the second arithmetic circuit in the latter stage of the operation directly relate to the type and quantity of the fluorescent materials in the light path of the measurement, the configuration, reflection rate, lighting method for the sample containers used for the measurement. Therefore, it should be better originally that linear regression of data of fluorescence derived from the fluorescent materials should be made after the data correction processing. However, if true increasing rate of the fluorescent materials is finally calculated by the structure of the present invention, the number of corrections will not increase even if the data measuring points increase. Moreover, the change of the correction parameters corresponded to changing the fluorescent materials emitting fluorescence by enzyme reactions is easily attainable. Furthermore, the number of data before the correction is very few compared with that of the method, with which the correction is made for each actually measured data. The invention is advantageous when the large storage of data before the correction is required. When constructing the apparatus, it is possible to localize the data processing circuit by dividing the circuit into parts before and after the correction. Thus, the structure has such advantages that the development of the system (such as programs) or maintenance is easy, and especially such advantage that functionability of the apparatus is easily increased by adding the aforementioned correction processing circuit to an existing apparatus having no correction functions.

One of the processing examples by the aforementioned second arithmetic circuit of the data processor is given in the following.

When the absorption of the excited light by the fluorescent materials is comparatively small (several %-ten-odd %), actual errors can be neglected by the following equation, wherein terms up to the second order is taken into consideration.

(Actual fluorescence intensity)=(Virtual fluorescence intensity)−h × (virtual fluorescence intensity)$^2$ (h=correction factor)

In the above equation, virtual fluorescence intensity is based on the supposition that the ratio of absorption of the excited light can be neglected. It is assumed that the quantity of actual fluorescent materials is in proportion to the aforementioned virtual fluorescence intensity and the quantity of virtual fluorescent materials is in proportion to the actually measured fluorescence intensity. Therefore, in the same way, the quantity and density of fluorescent materials are shown in the following equation.

(k, l mean correction factors)

(Apparent fluorescent materials)=(Actual quantity of fluorescent materials)−k × (Actual quantity of fluorescent materials)$^2$ (Apparent density of fluorescent materials)=(Actual density of fluorescent materials)−l × (Actual density of fluorescent materials)$^2$ In the above equations, when the increasing rate of fluorescent materials is r, the quantity of fluorescent materials at zero time is s, the quantity of fluorescent materials at the arbitrary time is x, and prime (') is affixed to the apparent value, then the quantity of apparent fluorescent materials x' after t time from zero time is shown in the following equations.

$$x = rt + s \quad \text{(Equation 1)}$$

$$x' = x - kx^2 \quad \text{(Equation 2)}$$

Linear regression to x' can be determined by minimizing the following conditions for adding to r' and s'.

$$\sum_{i=1}^{n} \{x_i' - (r't_i + s')\}^2 \quad \text{(Equation 3)}$$

(In this case, suppose data sampling is made from the initiating time of actual data measurement $t_1$ (i=1) to the finishing time of actual data measurement $t_n$ (i=n) at equal intervals of time, and the quantity of apparent fluorescent materials at each sampling point is shown as $x_i'$).

The equation 3 is partially differentiated by r' and s' and the conditions are shown as the equations 4 and 5.

$$\sum_{i=1}^{n} x_i' t_i - r' \sum_{i=1}^{n} t_i^2 - s' \sum_{i=1}^{n} t_i = 0 \quad \text{(Equation 4)}$$

$$\sum_{i=1}^{n} x_i' - r' \sum_{i=1}^{n} t_i - s' \sum_{i=1}^{n} 1 = 0 \quad \text{(Equation 5)}$$

In this processing example, the process to determine r' and s' from the aforementioned equations 4 and 5 corresponds to the process of the first arithmetic circuit under the present invention.

In order to lead to the correction equation, substitute equations 1 and 2 for equations 4 and 5 described above, and then eliminate s' from the equations. Neglect the second and higher order terms in ks and the third and higher order terms in kr':

$$r = (1 + 2ks)[1 + (t_1 + t_n) kr' + 2\{(t_1 + t_n) kr'\}^2] r' \quad \text{(Equation 6)}$$

($t_1$: Initiating time of actual data measurement
$t_n$: Finishing time of actual data measurement)

Furthermore, substitute s' for s in equation 6 is made approximately. Then, the equation 6 described above can be shown as the equation 7.

$$r = (1 + 2ks')[1 + (t_1 + t_n) kr' + 2\{(t_1 + t_n) kr'\}^2] r' \quad \text{(Equation 7)}$$

According to the equation 7, the increasing rate of actual fluorescent materials corrected for the error by the absorption of the excited light can be determined by the increasing rate of apparent fluorescent materials, the quantity of apparent fluorescent materials at zero time, and data of detection initiating and finishing time of fluorescence, which corresponds to the second arithmetic circuit. When the quantity of fluorescent materials at zero time is small enough in the equation 7, $(1+2ks')$ can be treated as 1.

Besides the equation 7, a formula for the correction may be expressed in other forms in the similar point of view or in a different approximation.

Needless to say, the first and second arithmetic circuits of the data processor under the present invention can be a digital process circuit or an analog process circuit using an integrator. In the analog process circuit, actual measurement is performed continuously. Therefore, if $$\int_{t_l}^{t_n}$$

is put in place of $$\sum_{i=1}^{n},$$

then:

$$r = (1+2ks)\,[r' + (t_1+t_n)\,kr^2]$$

is given, and if the right side member r is given as $$r = r' + (t_1+t_n)\,kr'^2$$

H and higher order terms concerning $r'^2$ are omitted, the equation 6 described in the above mentioned digital process can be obtained. With the analog circuit, exact correction processing can be attained by the feedback circuit. (But s approximated to s'.)

DESCRIPTION OF THE PREFERRED EMBODIMENTS

The preferred embodiments of the present invention will be described referring to the drawings:

FIG. 1 shows a typical structure of one of the preferred embodiments of the present invention. In this figure, for reasons of convenience in drawing, the direction of the source light radiation to a sample container 5 and that of extracting of the emitted light are shown in opposite. Actually, the source light radiation and the emission of the fluorescence for the sample container in FIG. 5 are performed by the top-to-top configuration.

In this figure, 1 shows pulse power supply which supplies source voltage as pulse signal b to a fluorescent tube 2 for switching light. Light rays c from condenser lens 4 pass through filter on the excitation side 3 and the condenser lens 4 for radiating the excitation light within the sample container 5. The filter on the excitation side 3 in the example is used for selectively transmitting the light rays of around 365 nm in conformity with the characteristic of the fluorescent materials (4-methyl umbelliferone) which will be described later.

In the sample container, antigen-antibody reaction enzyme complex which is produced by the immunoreactivity and substrate solution are filled. Fluorescent materials are increasingly produced with the passage of time. In this example, alkaline phosphatase is used as enzyme, 4-methyl umbelliferylphosphate as substrate, and 4-methyl umbelliferone as reaction product. Alkaline phosphates resolves 4-methyl umbelliferylphosphate into 4-methyl umbelliferone under alkaline conditions of approximate pH 10. Moreover, the 4-methyl umbelliferone absorbs the excited light having wavelength or around 365 nm and emits light rays of 450–500 nm.

On the other hand, 4-methyl umbelliferylphosphate absorbs no light rays of 365 nm and emits no fluorescence even if the excited light of 365 nm is radiated within the sample container and accordingly has no relation with the measurement of fluorescence.

Therefore, when the light ray of around 365 nm (the excited light) is radiated within the sample container 5, the increase in the intensity of fluorescence derived from the 4-methyl umbelliferone is detected when 4-methyl umbelliferone is produced and increased in conformity with the progress of enzyme reactions described above.

Considerations should be given to the absorption of the excited light due to the following reasons. Light rays of 400 nm or longer in wavelength are not absorbed by 4-methyl umbelliferone or 4-methyl umbelliferylphosphate, but 4-methyl umbelliferone absorbs light rays of 365 nm. Absorption of light rays by 4-methyl umbelliferone shows molar extinction coefficient of $e = \text{approx. } 1.4 \times 10^4$. Therefore, when the density is high, absorption of the radiated light (the excited light) with 4-methyl umbelliferone increases in quantity. Thus, some part of the excited light does not reach to the bottom of the sample container. As the result of it, the influence on the detected value is not negligible.

When the fluorescence is emitted by the radiation of the excited light as described above, the fluorescence passes through the fluorescence lens 6 and the filter on the fluorescence side 7, and is received by the light receiving sensor 8.

Signals originated from the fluorescence which had been received and actually measured by the light receiving sensor 8 are detected by phase sensitive detector 10 through amplifier 9 and are converted into signal e to data processing circuit 20 after removal of the influence of the background light and others. In this example of the present invention, signal a synchronizing with the clock signal of switching light of the fluorescent tube 2 is inputted into the phase sensitive detector 10 for the purpose of the phase sensitive detection.

Figure 2:
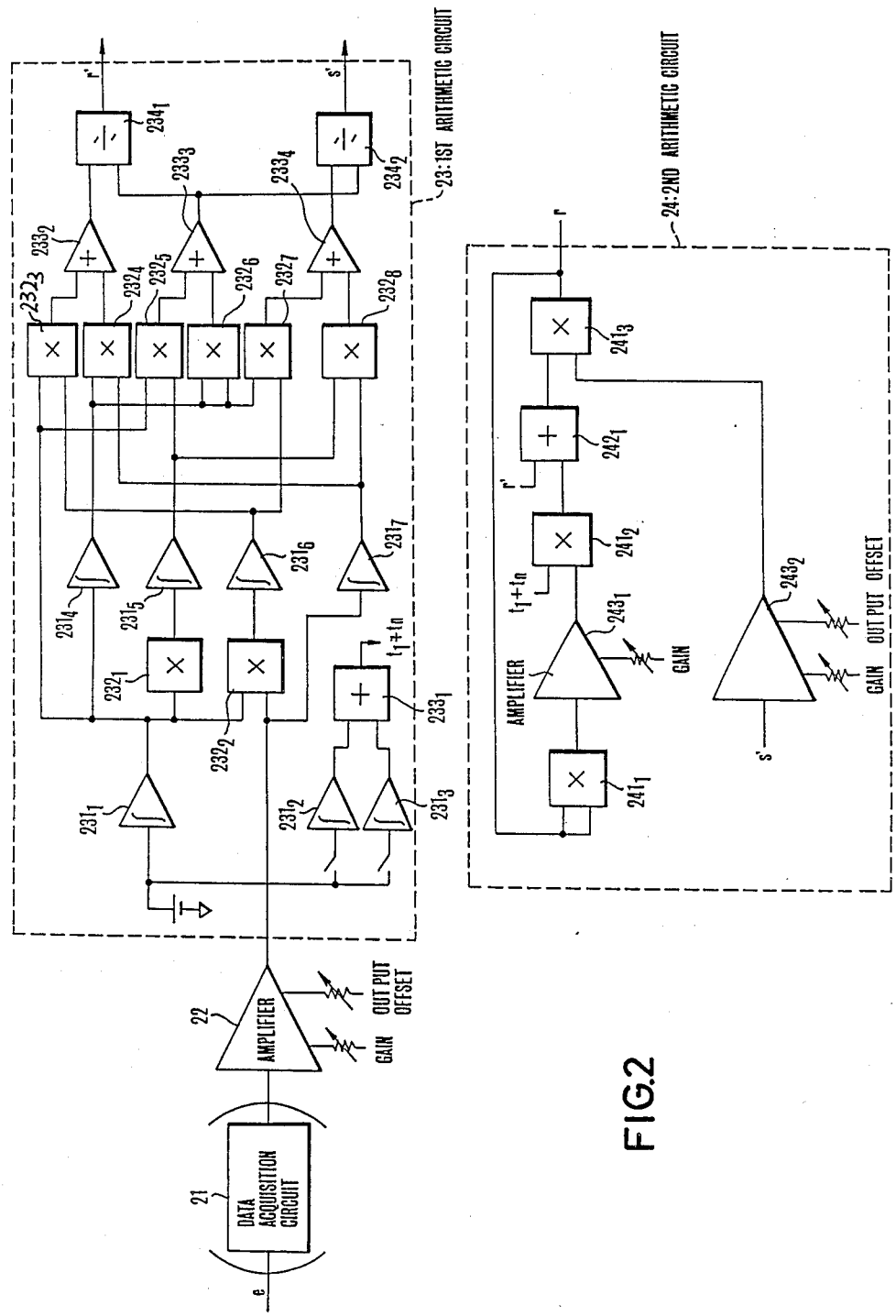
FIG. 2 is a drawing illustrating one structural example of the data processing circuit.

FIG. 2 is a drawing of analog circuit showing a structural example of the data processing circuit 20. In this example, analog signal e as input signal is inputted from the phase sensitive detector 12 to be processed in accordance with the steps shown on the flow chart of FIG. 3 as is shown in the circuit of FIG. 2. Then, accordingly, actual increasing rate of fluorescent materials is determined.

In FIG. 2, 21 shows data acquisition circuit which serves as A/D converter for digital processing. This circuit is not required for analog process circuit. 22 shows an amplifier served as a circuit for the 2nd step in FIG. 3, which in this example converts signals from data acquisition circuit (the signal of the intensity of fluorescence) into signals of corresponding quantity of fluorescent materials (or the density of fluorescent materials) to output to the next stage arithmetic circuit.

Figure 3:
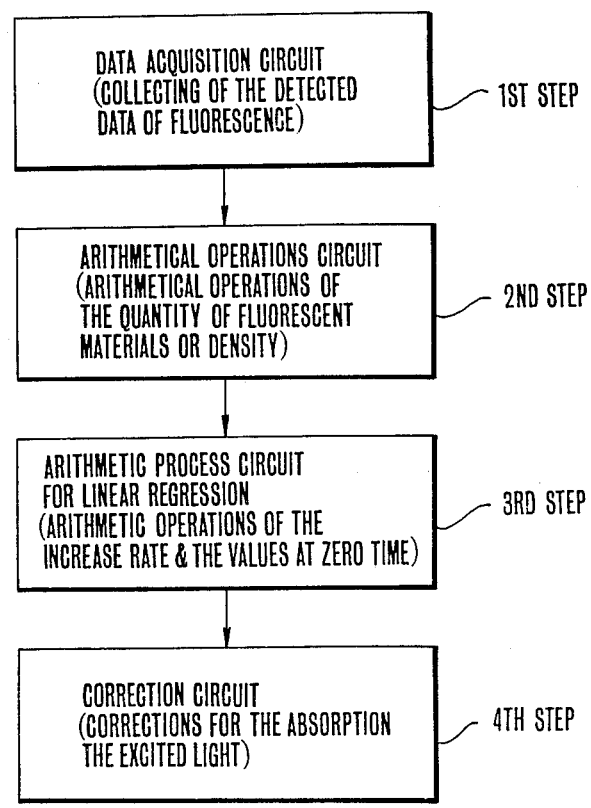
FIG. 3 is a drawing showing the summary of the process procedure for data processor.

Calculation of the increasing rate of apparent fluorescent materials and the quantity of fluorescent materials at zero time by linear regression operation in the 3rd step on FIG. 3 is done by 23 on FIG. 2, which constitutes the first arithmetic circuit in this embodiment of the present invention in conjunction with the amplifier 22 described above. The arithmetic circuit consists of integrators $231_1$–$231_7$, multipliers $232_1$–$232_8$, adders $233_1$–$233_4$, dividers $234_1$–$234_2$, forming linear regression arithmetic process circuit wherein r' is outputted from divider $234_1$ and s' from divider $234_2$.

24 in FIG. 2 forms the second arithmetic circuit for making corrections of the absorbed part of the excited light in the 4th step on FIG. 3. The second arithmetic circuit 24, in this example, consists of multipliers $241_1$–$241_3$, adder $242_1$, and amplifiers $243_1$ and $243_2$, and outputs the true increasing rate of fluorescent materials corrected by the multiplier $241_3$ on the basis of signals r' and s' from the first arithmetic circuit 23 described above.

A concrete method of the measurement will be given for the measuring apparatus for enzyme reaction rates which has a structure described above.

A sample of the mol number x is filled into a container 5 of depth d, whereupon the excited light is radiated, and consideration is given to the fluorescence intensity of fluorescent materials and absorption of the excited light. Suppose the light intensity of the excited light on the upper surface of the sample as $I_0$, and if the reflection from the bottom of the sample container is negligible (actually the reflection is negligible in a black container of the sample) then, the light intensity on the bottom is:

$$I_0 \cdot 10^{-y} \quad (y = -\epsilon dx/v)$$

and the difference $I_0 - I_0 \cdot 10^{-y}$ means the quantity of extinction by 4-methyl umbelliferone.

The intensity of fluorescence is in proportion to absorption quantity, then:

$$\text{(the intensity of fluorescence)} = k \cdot (I_0 - I_0 \cdot 10^{-y}) \quad \text{(Equation 8)}$$
$$= k \cdot I_0 \{\log 10 \cdot y - (\log 10 \cdot y)^2\}$$

Therefore, the relationship between apparent quantity of fluorescent materials and true quantity of fluorescent materials is:

$$x' = x - \log 10 \cdot \epsilon(d/v) x^2 \quad \text{(Equation 9)}$$
$$= x - k \cdot x^2 \quad \text{(Equation 10)}$$

In this case, k means correction coefficient and equals to $\log 10 \cdot \epsilon(d/v)$.

Suppose the diameter of the bottom of the sample container shown in FIG. 5 is 8 mm, and the sample solution in the cell is 200 ul. Then, when the sample solution is filled up to 4 mm in depth, and if xmol 4-methyl umbelliferone is filled in the 4 mm depth, then, $$k = 2.8 \times 10^4 \quad \text{from } \epsilon = \text{approx. } 1.4 \times 10^4$$

Figure 4:
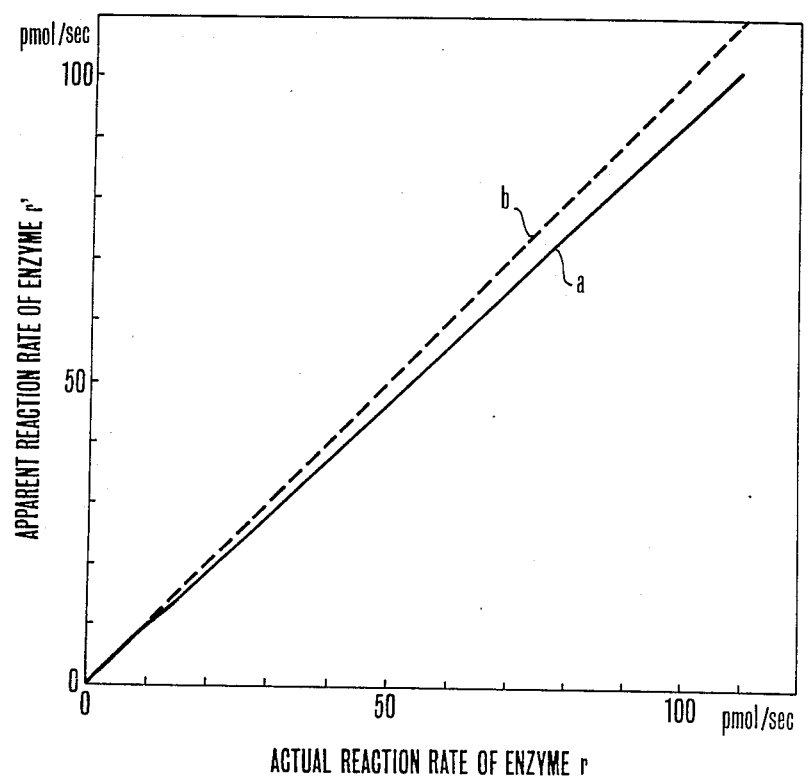
FIG. 4 is a drawing showing the relation between the actual increasing rate of fluorescent materials and the apparent increasing rate r' of fluorescent materials.

FIG. 4 shows one example of the measurement of enzyme reaction rate by the apparatus described above. In the measurement shown in this figure, the measurement is initiated at 10 seconds after the beginning of the enzyme reaction ($t_1 = 10$) and is finished at 110 seconds later ($t_n = 110$), the apparent quantity of fluorescent materials at the initiation of the enzyme reaction is s' ($<< 1.6$ nmol) and that of fluorescent materials at the end of the measurement is x' ($\leq 1.6$ nmol). However, the measurement was stopped at the time when the amount of fluorescent materials exceeded 1.6 nmol within 110 seconds after the initiation of the enzyme reaction.

In FIG. 4, a dotted line b is for comparing with an example in the embodiment of the present invention when the absorption of the excited light is neglected and the correction value is assumed to be zero. A line a shows the line measured by the apparatus under this invention, wherein the correction has significant values.

Needless to say, the present invention is not limited in the embodiments described above, but the data processor generally consists of circuits utilizing a micro computer. In that case, the structure of the program for the apparatus can also be based on the same point of view as described above. When an actual apparatus utilizes a digital processing circuit, the apparatus may be composed, for instance, of a local processor in charge of the circuit up to data acquisition circuit in the first arithmetic circuit (as for the example in FIG. 3, up to the second step or in the middle of the third step) and a main processor in charge of process of the rest.

As has been described above, the measuring apparatus for enzyme reaction rates under the present invention has advantages for measuring enzyme ranging from minute to large quantity, of which exact quantitative determination is demanded with least error of measurement. The aforementioned advantage can be attained by adding comparatively simple modifications to the conventional type of the measuring apparatus for enzyme reaction rates. Thus, accuracy in measurement improves greatly and the capacity of the circuits to be used becomes small.

Furthermore, the apparatus in the present invention has the advantages in that increasing of the frequency of the corrections is not required with the increase of the data measuring points and the change over of the correction parameters corresponding to changing the fluorescent materials which will emit fluorescence through enzyme reactions is easy in the second arithmetic circuit for the correction process. Moreover, the number of data before the correction is made becomes much fewer than that of the correction method for every measured data and it is advantageous to storing data before the correction is made.

In the construction of the apparatus, the possibility to divide and localize data processing circuits into parts before and after the corrections leads to easy development of the system (such as programs) and an advantage to maintenance. Besides that, leveling up of the functions of the apparatus is possible by adding the correction process circuit to the existing apparatus having no correction functions. As the result of it, the usefulness of the apparatus improves greatly.

What is claimed is:

1. A measuring apparatus for enzyme reaction rates comprising:

optical detection means for detecting in time series the intensity of fluorescence derived from fluorescent materials obtained through enzyme reactions, a first arithmetic circuit having time series signals of the intensity of the fluorescence detected by the optical detection means as an input for calculating apparent increasing rate of the fluorescent materials by utilizing a predetermined computation equation, and a second arithmetic circuit having an apparent increasing rate of the fluorescent materials computed through the first arithmetic circuit as an input information for calculating a true increasing rate of the fluorescent materials by utilizing a predetermined correction equation, wherein enzyme contributing to the aforementioned reaction is obtained through enzyme immunoreaction.

2. A measuring apparatus for enzyme reaction rates according to claim 1, wherein enzyme contributing to the enzyme reaction is obtained through enzyme immunoreaction.

* * * * *